United States Patent [19]

Duranleau et al.

[11] Patent Number: 4,529,822
[45] Date of Patent: Jul. 16, 1985

[54] PROCESS FOR THE PREPARATION OF FORMAMIDE COMPOUNDS

[75] Inventors: Roger G. Duranleau; Clifford L. Lambert, Jr., both of Georgetown, Tex.

[73] Assignee: Texaco, Inc., White Plains, N.Y.

[21] Appl. No.: 543,552

[22] Filed: Oct. 19, 1983

[51] Int. Cl.³ .............................................. C07C 102/00
[52] U.S. Cl. .................................. 564/132; 564/215; 564/217; 564/224
[58] Field of Search ................ 564/132, 215, 217, 224

[56] References Cited

U.S. PATENT DOCUMENTS 4,329,462  5/1982  Tamura et al. ................. 564/215 X

OTHER PUBLICATIONS

Saunders et al., CA 53:17879g, (1959).

Primary Examiner—Thomas A. Waltz
Attorney, Agent, or Firm—Robert A. Kulason; Jack H. Park; Cynthia L. Kendrick

[57] ABSTRACT

This invention relates to preparing formamide compounds in a process which comprises reacting an amine with a formylalkanolamine in the presence of carbon monoxide in which the mole ratio of amine to formylalkanolamine ranges from 0.2:1 to 5:1. The reaction is conducted at a temperature ranging from about 50° to 300° C. and a pressure ranging from about 100 to 10,000 psig. The amine employed in the reaction has the formula:

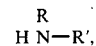

wherein R' is hydrogen, an alkyl group of 1 to 10 carbon atoms, cyclohexyl, or —R''—O—R''', wherein R'' is a divalent alkylene group of 2 to 4 carbon atoms and R''' is an alkyl group of 1 to 3 carbon atoms; and R is hydrogen or an alkyl group of 1 to 10 carbon atoms. The formylalkanolamine employed in the reaction has the formula:

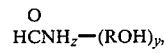

wherein R is an alkylene group of 1 to 3 carbon atoms, z is 0 or 1 and y is 1 or 2 and the sum of y and z is 2.

20 Claims, No Drawings

PROCESS FOR THE PREPARATION OF FORMAMIDE COMPOUNDS

BACKGROUND OF THE INVENTION

Field of the Invention

Formamides comprise a class of valuable commercial compounds having uses as solvents in the chemical process industry for the manufacture of acrylic fibers and polyurethane and in the manufacture of pharmaceutical products and pesticides. In general, formamides are prepared by reacting the corresponding amine with carbon monoxide in the presence of a metallic catalyst to promote the desired reaction. A disadvantage of the process is the difficulty of separating the formamide product from the reaction mixture containing the metallic catalyst. It has also been known to prepare formamides by reacting the corresponding amine with an ester such as methyl formate. Neither of these known processes are entirely satisfactory.

An improved method for preparing formamides which is not dependent on the use of a metal catalyst and which overcomes the differences of the known process has now been discovered.

It is an object of this invention to provide an efficient process for the carbonylation of amines to formamides.

It is a further object of this invention to provide a novel process in which the carbonylation of amines is effected in the absence of a metallic catalyst.

Disclosure Statement

British Pat. No. 925,588 discloses the preparation of dimethyl formamide by carbonylating dimethylamine in a solution of an aliphatic alcohol and in the presence of an alkali metal alcoholate catalyst.

U.S. Pat. No. 4,230,636 discloses the preparation of dimethyl formamide by carbonylating a mixture of mono-, di- and trimethyl amine in the presence of iron metal or an iron compound such as the oxide, hydroxide or iron carbonyl compound.

U.S. Pat. No. 4,098,820 discloses a method for the preparation of a formamide in which carbon monoxide is reacted with a nitrogen containing compound from the group consisting of ammonia, primary alkylamine and secondary alkylamine in the presence of a methanolic solution of an alkali metal or an alkaline earth metal methoxide catalyst.

SUMMARY OF THE INVENTION

This invention relates to preparing formamide compounds in a process which comprises reacting an amine with a formylalkanolamine in the presence of carbon monoxide in which the mole ratio of amine to formylalkanolamine ranges from 0.2:1 to 5:1. The reaction is conducted at a temperature ranging from about 50° to 300° C. and a pressure ranging from about 100 to 10,000 psig. The amine employed in the reaction has the formula:

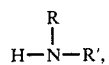

wherein R' is hydrogen, an alkyl group of 1 to 10 carbon atoms, cyclohexyl, or —R"—O—R'", wherein R" is a divalent alkylene group of 2 to 4 carbon atoms and R'" is an alkyl group of 1 to 3 carbon atoms; and R is hydrogen or an alkyl group of 1 to 10 carbon atoms.

The formylalkanolamine employed in the reaction has the formula:

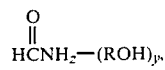

wherein R is an alkylene group of 1 to 3 carbon atoms, z is 0 or 1 and y is 1 or 2 and the sum of y and z is 2.

DETAILED DESCRIPTION OF THE INVENTION

This invention relates to preparing formamide compounds in a process in which an amine is reacted with a formylalkanolamine in the presence of carbon monoxide, with said amine having the formula:

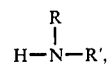

wherein R' is hydrogen, an alkyl group of 1 to 10 carbon atoms, cyclohexyl, or —R"—O—R'", wherein R" is a divalent alkylene group of 2 to 4 carbon atoms and R'" is an alkyl group of 1 to 3 carbon atoms; and R is hydrogen or an alkyl group of 1 to 10 carbon atoms; and with said formylalkanolamine having the formula:

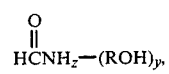

wherein R is an alkylene group of 1 to 3 carbon atoms z is 0 or 1 and y is 1 or 2 and the sum of y and z is 2.

The formylalkanolamine is prepared in accordance with applicants' copending application Ser. No. 514,712 which is hereby incorporated by reference. The formylalkanolamine is prepared by reacting an alkanolamine, such as monoethanolamine and diethanolamine, with carbon monoxide under conditions of high temperature and pressure. The preferred formylalkanolamines for use in the instant invention are formyldiethanolamine and formylethanolamine. The formylalkanolamine reactant employed in the reaction can, if desired, be formed in situ in the reaction mixture. Also, the corresponding alkanolamine produced when the amine reactant is carbonylated (or any unreacted formylalkanolamine) can be easily separated by distillation means from the formed reaction product, and as part of a continuous recycling process, the alkanolamine can be reacted with carbon monoxide to again form the specified formylalkanolamine.

The amines employed in the instant invention are primary or secondary amines. The amine substituents can include straight-chained or branched alkyl groups of 1 to 10 carbon atoms, cyclohexyl, and alkylenealkoxy groups in which the alkylene group comprises 2 to 4 carbon atoms and the alkyl group comprises 1 to 3 carbon atoms. Suitable amines include those having one or two substituents comprising branched or straight-chain alkyl groups such as methylamine, dimethylamine, ethylamine, diethylamine, propylamine, dipropylamine, butylamine, dibutylamine, and the like; isopropylamine, sec-butylamine, isobutylamine, sec-pentylamine, isopentylamine, and the like. When both amine substituents are alkyl groups, each alkyl group preferably comprises from 1 to 5 carbon atoms. Suitable amines also include those having a substituent comprising an alkylene-alkoxy group such as 2-methoxy ethyl, 2-ethoxy ethyl, 2-propxy ethyl, 3-methoxy propyl, 3-ethoxy propyl, 3-propxy propyl, and the like. The preferred amines include ammonia, dimethylamine, ethylamine, sec-butylamine, isopropylamine, 3 methoxy propylamine, cyclohexylamine, methylamine, and diethylamine.

The amine and the formylalkanolamine are in the instant invention reacted in a mole ratio of amine to formylalkanolamine of 0.2:1 to 5:1. Preferably, the amine and formylalkanolamine reactants are reacted in equal mole concentrations.

The reaction occurs at temperatures ranging from 60° to 300° C. and pressures ranging from 100 to 3000 psig. The preferred temperature range is 100° to 250° C. and the preferred pressure range is 200 to 5000 psig, with the most preferred temperature range being 40° to 200° C. and the most preferred pressure range being 400 to 2000 psig.

The Examples below demonstrate that formamide compounds can be formed in rapid fashion by reacting in approximately equal mole ratios formylalkanolamine and the specified amine reactant.

EXAMPLE I

Production of Dimethylformamide

To 90.0 grams of dimethyamine (2.0 moles), 210 grams of diethanolamine (2.0 mole) were added, and the mixture was placed in a stirred autoclave maintained at a temperature of 150° to 155° C. and a carbon monoxide pressure of 1125 psig. Periodically, the autoclave was repressurized with carbon monoxide so that the system pressure was maintained at a pressure of from 1125 to 1310 psig. After 11 hours, the reaction was stopped. The 345 grams of liquid product recovered was shown by NMR analysis to comprise starting material, formyldiethanolamine and dimethylformamide (83% of theory). The product was partially distilled at atmospheric pressure and the 79 grams of overhead fraction (B.P. 146°–156° C.) was shown by NMR analysis to be dimethylformamide. The corresponds to a yield of 49.3%.

The reaction was repeated with the temperature maintained at 200° C. and the carbon monoxide pressure maintained at 1200 psig. After 4 hours, the reaction was stopped. The product was shown by NMR analyis to comprise formyldiethanolamine and dimethylformamide (92% of theory).

EXAMPLE II

Production of Dimethylformamide

To 270 grams of dimethylamine (6.0 moles), 105 grams of diethanolamine (1.0 mole) were added and the mixture was placed in a stirred autoclave maintained at a temperature of 150° to 155° C. and a carbon monoxide pressure of 1625 psig. After 5 hours, no carbon monoxide was consumed and no dimethylformamide was formed.

EXAMPLE III

Production of Dimethylformamide

To 90 grams of dimethylamine (2.0 moles), 534 grams (6.0 mole) of formylethanolamine were added, and the mixture was placed in a stirred autoclave maintained at a temperature of 150° to 155° C. and a carbon monoxide pressure of 1510 psig. After 15 hours, the reaction was stopped and the product was removed from the autoclave and distilled at 20 mm Hg. The 143 grams of overhead product (B.P. 64°–72° C.) was shown by NMR analysis to be dimethylformamide. This corresponds to a yield of 98%.

EXAMPLE IV

Preparation of Formamide

To 268 grams of ammonia (4.0 moles), 210 grams of diethanolamine (2.0 moles) were added, and the mixture was placed in a stirred autoclave maintained at a temperature of 150° to 155° C. and a carbon monoxide pressure of 1135 psig. The carbon monoxide pressure was increased to 2330 psig, and, then, over an 8-hour period, the pressure was reduced to 1510 psig. After cooling overnight, the autoclave was again repressurized to a pressure of 1125 psig and heated to a temperature of 150° to 155° C. The carbon monoxide pressure was increased to 2225 psig, and, then, over a 7-hour period, the pressure was reduced to 1150 psig and then increased to 1650 psig. After the reaction was stopped, the product was removed. The product as shown by NMR analysis comprised formamide (60% of theory). The product was distilled at atmospheric pressure and the 48 grams of overhead fraction was shown by NMR analysis to be formamide. This corresponds to a yield of 26.7%.

EXAMPLE V

Preparation of Formamide

To 85.0 grams of ammonia (5.0 moles), 210 grams of diethanolamine (2.0 moles) were added, and the mixture placed in a stirred autoclave maintained at a temperature of 150° to 155° C. and a carbon monoxide pressure of 1535 psig. Periodically, the autoclave was repressurized with carbon monoxide so as to maintain a system pressure of 1500 psig. After 24 hours, there was no further carbon monoxide absorption and the contents of the autoclave were removed. The 476 grams of product were shown by proton NMR analysis to comprise formyldiethanolamine and formamide (90% of theory).

EXAMPLE VI

Preparation of Ethylformamide

To 120 grams of ethylamine (2.67 mole), 399 grams of formyldiethanolamine (3.0 moles) were added, and the mixture was placed in a stirred autoclave maintained at a temperature of 150° to 155° C. and a carbon monoxide pressure of 1250 psig. Periodically, the autoclave was repressurized with carbon monoxide so as to maintain a system pressure of 1250 psig. After 12 hours, the 566 grams of liquid product was removed from the autoclave and distilled at 20 to 25 mm Hg. The 154 grams of overhead product was showed by proton NMR analysis to be ethylformamide. This corresponds to a yield of 79%.

EXAMPLE VII

Preparation of Sec-butylformamide

To 146 grams of sec-butylamine (2.0 moles), 399 grams of formyldiethanolamine (3.0 moles) were added, and the mixture was placed in a stirred autoclave maintained at a temperature of 150° to 155° C. and a carbon monoxide pressure of 1475 psig. Periodically, the system was repressurized with carbon monoxide so as to maintain a system pressure of 1475 psig. After 16 hours, the reaction was stopped and the 575 grams of liquid product were distilled at 30 to 35 mm Hg. The overhead fraction (185.4 g) was found by proton NMR analysis to be sec-butylformamide. This corresponds to a yield of 91.7%.

EXAMPLE VIII

Preparation of Isopropylformamide Employing Recycled Formylalkanolamine

To 177 grams of isopropylamine (1.3 moles), the bottom fraction from Example 4 was added, and the mixture was placed in a stirred autoclave maintained at a temperature of 150° to 155° C. and a carbon monoxide pressure of 1540 psig. Periodically, the autoclave was repressurized with carbon monoxide so as to maintain a system pressure of 1540 psig. After the reaction was stopped, the 470 grams of liquid product was removed and distilled at 10 mm Hg. The 113 grams of overhead fraction (boiling point 92°–99° C.) was shown by proton NMR analysis to be isopropylformamide. This corresponds to a yield of 99.6%.

EXAMPLE IX

Preparation of 3-methoxy Propylformamide

To 158 grams of 3-methoxy propylamine (1.77 moles), 346 grams of formylethanolamine (4.0 moles) were added, and the mixture was placed in a stirred autoclave maintained at a temperature of 150° to 155° C. and a carbon monoxide pressure of 1500 psig. During the 8-hour period of reaction, the carbon monoxide pressure was maintained at 1580 psig. After the reaction was stopped, the contents of the autoclave were removed and distilled at 10 to 20 mm Hg. The 198 grams of overhead fraction (B.P. 125° to 146° C.) was shown by NMR analysis to be 3-methoxy propylformamide. This corresponds to a yield of 96%.

EXAMPLE X

Preparation of Cyclohexylformamide

To 198 grams of cyclohexylamine (2.0 grams), 399 grams of formyldiethanolamine (3.0 mole) were added, and the mixture was placed in a stirred autoclave maintained at a temperature of 150° to 155° C. and a carbon monoxide pressure of 1260 psig. After the reaction was stopped, the contents of the autoclave were removed and distilled at 15 mm Hg. The 256 grams of overhead fraction (B.P. 155°–161° C.) was shown by proton NMR analysis to be cyclohexylformamide. This corresponds to yield of 100%.

EXAMPLE XI

Preparation of Methylformamide

To 92 grams of methylamide (3.0 moles) 309 grams of formyldiethanolamine (3.0 mole) were added, and the mixture was placed in a stirred autoclave maintained at a temperature of 150° to 155° C. and a carbon monoxide pressure of 1400 psig. Periodically, the autoclave was repressurized with carbon monoxide to maintain a system pressure of 1400 psig. After 16 hours there was no further consumption of carbon monoxide and the contents of the autoclave were removed and distilled at 33 mm Hg. The 171 grams of overhead product (B.P. 115°–122° C.) was shown by NMR analysis to be methylformamide. This corresponds to a yield of 96%.

EXAMPLE XII

Preparation of Diethylformamide

To 146 grams of diethylamine (2.0 moles), 356 grams of formylethanolamine (4.0 moles) were added, and the mixture was placed in a stirred autoclave maintained at a temperature of 150° to 155° C. and a carbon monoxide pressure of 1800 psig. Periodically, the autoclave was repressurized with carbon monoxide and, during the final 4 hours of reaction, the carbon monoxide pressure was maintained at a constant pressure of 1500 psig. After the reaction was stopped, the 554 grams of liquid product were removed and NMR analysis indicated that the product comprises diethylformamide (99% of theory).

EXAMPLE XII

Preparation of Diethylformamide

To 219 grams of diethylamine (3.0 moles), 399 grams of formyldiethylanolamine (3.0 moles) were added, and the mixture placed in a stirred autoclave maintained under the same conditions as in Example XII. After the reaction was stopped, the 676 grams of liquid product recovered were distilled at 50 mm Hg. The 289 grams of overhead fraction (B.P. 94° to 97° C.) was shown by NMR analysis to be diethylformamide. This corresponds to a yield of 95.4%.

EXAMPLE XIII

Preparation of Dimethylformamide Employing Recycled Formylalkanaolamine

To 141 grams of diethylamine (1.93 moles), the bottom fraction of Example IX B was added, and the mixture was placed in a stirred autoclave maintained at the same pressure and temperature conditions as in Example IX B. After the reaction was stopped, the 480 grams of liquid product were removed and distilled at 50 mm Hg. and the 197 grams of overhead fraction was shown by overhead analysis to be diethylformamide. This corresponds to a yield of 100%.

What is claimed:

1. A process for the preparation of a formamide which comprises reacting an amine with a formylalkanolamine in the presence of carbon monoxide at a temperature ranging from about 50° to 300° C., a pressure ranging from about 100 to 10,000 psig, and a mole ratio of said amine to said formylalkanolamine from 0.2:1 to 5:1, respectively, said amine having the formula:

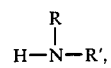

wherein R' is selected from the group consisting of hydrogen, an alkyl group of 1 to 10 carbon atoms, a cyclohexyl, or —R"—O—R'", wherein R" is a divalent alkylene group of 2 to 4 carbon atoms and R'" is an alkyl group of 1 to 3 carbon atoms; and R is selected from the group consisting of hydrogen or an alkyl group of 1 to 10 carbon atoms; and said formylalkanolamine having the formula:

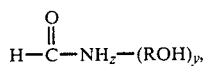

wherein R is an alkylene group of 1 to 3 carbon atoms, z is 0 or 1 and y is 1 or 2 and the sum of y and z is 2.

2. A process according to claim 1 wherein R and R' are both alkyl groups of 1 to 5 carbon atoms.

3. A process according to claim 1 wherein the temperature employed ranges from 100° to 250° C. and the pressure employed ranges from 200 to 5,000 psig.

4. A process according to claim 1 wherein the temperature employed ranges from 140° to 200° C. and the pressure employed ranges from 400 to 2,000 psig.

5. A process according to claim 1 wherein the amine is dimethylamine.

6. A process according to claim 1 wherein the amine is ammonia.

7. A process according to claim 1 wherein the amine is ethylamine.

8. A process according to claim 1 wherein the amine is sec-butylamine.

9. A process according to claim 1 wherein the amine is isopropylamine.

10. A process according to claim 1 wherein the amine is 3-methoxypropylamine.

11. A process according to claim 1 wherein the amine is cyclohexylamine.

12. A process according to claim 1 wherein the amine is methylamine.

13. A process according to claim 1 wherein the formylalkanolamine is formyldiethanolamine.

14. A process according to claim 1 wherein the formylalkanolamine is formylethanolamine.

15. A process for preparing formamide which comprises reacting ammonia with a formylalkanolamine selected from the group consisting of formyldiethanolamine and formylethanolamine in the presence of carbon monoxide at a temperature ranging from 100° to 250° C. and a pressure ranging from 200 to 5,000 psig, and a mole ratio of said amine to said formylalkanolamine ranging from 0.2:1 to 5:1, respectively.

16. A process according to claim 14 wherein the formylalkanolamine is formyldiethanolamine.

17. A process according to claim 14 wherein the formylalkanolamine is formylethanolamine.

18. A process for preparing dimethylformamide which comprises reacting dimethylamine with a formylalkanolamine selected from the group consisting of formyldiethanolamine and formylethanolamine in the presence of carbon monoxide at a temperature ranging from 100° to 250° C. and a pressure ranging from 200 to 5,000 psig and a mole ratio of said amine to said formylalkanolamine ranging from 0.2:1 to 5:1, respectively.

19. A process according to claim 17 wherein the formylalkanolamine is formyldiethanolamine.

20. A process according to claim 17 wherein the formylalkanolamine is formylethanolamine.

* * * * *